(12) United States Patent
Lerebour et al.

(10) Patent No.: US 10,307,365 B2
(45) Date of Patent: ***Jun. 4, 2019

(54) **COSMETIC USE OF A GERANIOL-RICH ESSENTIAL OIL OF *SATUREJA MONTANA* AS DEODORANT ACTIVE AGENT**

(71) Applicant: L'OREAL, Paris (FR)

(72) Inventors: Géraldine Lerebour, Les Loges (FR); Pierre Lartaud, Eurre (FR); Bertrand Lacroix, Villejuif (FR)

(73) Assignee: L'OREAL, Paris (FR)

( * ) Notice: Subject to any disclaimer, the term of this patent is extended or adjusted under 35 U.S.C. 154(b) by 103 days.

This patent is subject to a terminal disclaimer.

(21) Appl. No.: 14/785,962

(22) PCT Filed: Apr. 14, 2014

(86) PCT No.: PCT/EP2014/057485
§ 371 (c)(1),
(2) Date: Oct. 21, 2015

(87) PCT Pub. No.: WO2014/173712
PCT Pub. Date: Oct. 30, 2014

(65) Prior Publication Data
US 2016/0067173 A1  Mar. 10, 2016

(30) Foreign Application Priority Data

Apr. 26, 2013  (FR) ..................... 13 53817

(51) Int. Cl.
| | |
|---|---|
| A61K 8/92 | (2006.01) |
| A45D 34/04 | (2006.01) |
| A61Q 15/00 | (2006.01) |
| A61Q 17/00 | (2006.01) |
| B05B 11/00 | (2006.01) |
| B65D 83/14 | (2006.01) |

(52) U.S. Cl.
CPC ............ *A61K 8/922* (2013.01); *A45D 34/041* (2013.01); *A61Q 15/00* (2013.01); *A61Q 17/005* (2013.01); *B05B 11/3042* (2013.01); *B65D 83/752* (2013.01); *A61K 2800/87* (2013.01); *A61K 2800/874* (2013.01)

(58) Field of Classification Search
CPC ....... A61K 8/922; A61Q 15/00; A61Q 17/005
See application file for complete search history.

(56) References Cited

U.S. PATENT DOCUMENTS

2011/0223222 A1* 9/2011 Spyros Botsaris ...... A61K 8/34
424/401

FOREIGN PATENT DOCUMENTS

EP  0433132 A1  6/1991

OTHER PUBLICATIONS de Oliveira et al., "Antimicrobial activity of *Satureja montana* L. essential oil against Clostridium perfringens type A inoculated in mortadella-type sausages formulated with different levels of sodium nitrite", 2011, International Journal of Food Microbiology, vol. 144, pp. 546-555.*

Marin et al., "Antioxidative, antibacterial and antifungal activity of the essential oil of wild-growing *Satureja montana* L. from Dalmatia, Croatia", Flavour Fragr. J., 2012, 27, 216-223.

Fraternale et al., "Chemical Composition and antifungal Activity of the Essential Oil of *Satureja montana* from Central Italy", Chemistry of Natural Compounds, vol. 43, No. 5, 2007, pp. 622-624.

Mirjana et al., "Chemical Composition and Antimicrobial Variability of *Satureja montana* L. Essential Oils Produced During Ontogenesis", Medicinal & Aromatic Plants Abstracts, Scientific Publishers, New Delhi—India, vol. 27, No. 2, Feb. 28, 2005.

Derbre et al., "Comment venir a bout des mycoses", Actualities Pharmaceutiques, Unions Techniques Intersyndicales Pharmaceutiques. Paris FR, vol. 49, No. 495, Apr. 1, 2010.

Pepeljnjak et al., "Antimicrobial Activity of the Ethanolic Extract of *Satureja montana* ssp. *montana*", Actal Pharn. 49 (1999) 65-69.

* cited by examiner

*Primary Examiner* — Michael B. Pallay
(74) *Attorney, Agent, or Firm* — Poisinelli PC

(57) ABSTRACT

Provided is a cosmetic use, as deodorant active agent, of an essential oil of *Satureja montana* comprising more than 60% by weight of geraniol and more than 5% by weight of trans-β-caryophyllene, and in particular an essential oil of *Satureja montana* L. ssp. *variegata* or *Satureja Montana* var. *citrodoria* oil. Also provided is a cosmetic method for treating human body odors, in particular the armpits or feet, which comprises applying, to human keratin materials, at least one *Satureja montana* essential oil comprising more than 60% by weight of geraniol and more than 5% by weight of trans-β-caryophyllene, and in particular an essential oil of *Satureja montana* L. ssp. *variegata* or *Satureja Montana* var. *citrodoria* oil or a composition containing same in a cosmetically acceptable medium.

9 Claims, No Drawings

COSMETIC USE OF A GERANIOL-RICH ESSENTIAL OIL OF *SATUREJA MONTANA* AS DEODORANT ACTIVE AGENT

CROSS REFERENCE TO RELATED APPLICATIONS

This application is a National Phase filing under 35 U.S.C. § 371 of PCT/EP2014/057485 filed on Apr. 14, 2014; and this application claims priority to Application No. 1353817 filed in France on Apr. 26, 2013, under 35 U.S.C. § 119. The entire contents of each application are hereby incorporated by reference.

The present invention relates to the cosmetic use, as deodorant active agent, of an essential oil of *Satureja montana* comprising more than 60% by weight of geraniol and more than 5% by weight of trans-β-caryophyllene, in particular of *Satureja montana* L. ssp. variegate (or *Satureja Montana* var. citrodoria oil), and more particularly in a composition comprising a cosmetically acceptable medium.

It also relates to a cosmetic method for treating human body odours, in particular of the armpits or feet, which consists in applying, to human keratin materials, at least one *Satureja montana* essential oil as defined previously or a composition containing same in a cosmetically acceptable medium.

Essential oils are products obtained from starting materials of plant origin (leaves, stems, flowers or whole plant, for example).

These essential oils can be obtained according to various processes, such as steam distillation, distillation or extraction by means of volatile solvents, in particular.

They are generally used for their odours, but also for their numerous pharmacological and/or cosmetic activities.

It is in particular known that some of them have an antibacterial and/or antifungal activity.

Furthermore, it is known that the unpleasant odours of perspiration are related in particular to the presence of microorganisms and more particularly *Corynebacterium xerosis*. In fact, sweat is in itself relatively non-odorous when it is secreted. It is the decomposition by bacteria via enzymatic reactions which produces malodorous compounds. Deodorant active agents have the specific function of reducing or preventing the formation of unpleasant odours.

The various systems proposed hitherto may be grouped into major families. Among them there are antibacterial substances that destroy the resident bacterial flora. The product most commonly used is Triclosan. There are also substances that reduce bacterial growth. Among these substances, mention may be made of transition-metal-chelating agents such as ethylenediaminetetraacetic acid (EDTA) or diethylenetriaminepentaacetic acid (DTPA).

However, these various treatments, applied to the skin of the armpits, have a tendency to bring about detrimental changes in the skin.

The need thus remains to find novel deodorant active agents which are effective and which do not have these drawbacks.

The plant *Satureja montana* is a plant of the family Lamiaceae. It is a hardy plant typical of the Mediterranean climate. This plant can in particular be found in the south of France, in particular in the southern half of the Drôme Department. Certain species originating from Bosnia are known, such as *Satureja montana* ssp *kitaibelli*. There is also *Satureja montana* L. ssp. variegata (Host) P. W. Ball (Lamiaceae), which is also known under the following botanical names: Dalmat or *Satureja variegata* Host, Fl. Austriac, more commonly known as lemon mountain sariette.

In the application EPO433132, it is known that sariette essential oils have an antibacterial activity on the bacteria Gram-positive activate and particularly on the microorganisms responsible for unpleasant body odours. Certain sariette essential oils as mountain sariette: *Satureia montana* oil comprising from 10 to 18% of para-cymene, from 0.2 to 2% limonene, from 8 to 18% of γ-terpinene, from 22 to 30% of carvacrol, from 12 to 20% of thymol and from 2 to 4% de β-caryophyllene, produce a strong unpleasant smell which can disturb the comfort of the consumer during its application on keratinous materials.

The need thus remains to find an essential of sariette having a good antibacterial activity on the microorganisms responsible for unpleasant body odours in particular *Corynebacterium xerosis*, without the drawbacks as evoked previously.

The inventors have demonstrated an antibacterial activity, with respect to the microorganisms responsible for unpleasant body odours, in particular *Corynebacterium xerosis*, of an essential oil of *Satureja montana* comprising more than 60% by weight of geraniol and more than 5% by weight of trans-β-caryophyllene, in particular an essential oil of *Satureja montana* L. ssp. variegata (or *Satureja Montana* var. citrodoria oil) such that it can be of use in a deodorant and/or antiperspirant cosmetic composition, and without producing a strong unpleasant smell which can disturb the consumer during its use.

The present invention relates to the cosmetic use, as deodorant active agent, of an essential oil of *Satureja montana* comprising more than 60% by weight of geraniol and more than 5% by weight of trans-β-caryophyllene, in particular an essential oil of *Satureja montana* L. ssp. variegata (or *Satureja Montana* var. citrodoria oil), and more particularly in a composition comprising a cosmetically acceptable medium.

It also relates to a cosmetic method for treating human body odours, in particular of the armpits or feet, which consists in applying, to human keratin materials, at least one *Satureja montana* essential oil as defined previously or a composition containing same in a cosmetically acceptable medium.

The present invention also relates to a composition comprising, in a cosmetically acceptable medium:
a) at least one essential oil of *Satureja montana* comprising more than 60% by weight of geraniol and more than 5% by weight of trans-β-caryophyllene, in particular of *Satureja montana* L. ssp. variegata, and
b) at least one deodorant active agent and/or at least one antiperspirant active agent.

It also relates in particular to a composition packaged
(i) in pressurized form in an aerosol device or in a pump-dispenser bottle;
(ii) in a device equipped with a perforated wall, in particular a grate;
(iii) in a device equipped with a ball applicator ("roll-on");
(iv) in the form of a stick; or
(v) in the form of a loose or compacted powder,
characterized in that it contains, in a physiologically acceptable medium, an essential oil of *Satureja montana* as defined previously.

The term "deodorant active agent" is intended to mean, in the context of the present invention, any active agent which, by itself alone, has the effect of masking, absorbing, improving and/or reducing the unpleasant odour resulting from the decomposition of human sweat.

The term "antiperspirant active agent" is intended to mean any substance which, by itself alone, has the effect of reducing the flow of sweat, of reducing the sensation on the skin of moisture associated with human sweat and of masking human sweat.

For the purposes of the present invention, the term "physiologically acceptable medium" is intended to mean a medium that is suitable for the topical administration of a composition.

A physiologically acceptable medium is preferentially a cosmetically or dermatologically acceptable medium, that is to say a medium which is devoid of unpleasant odour or appearance and which is entirely compatible with the topical administration route.

In the present case, where the composition is intended for topical administration, that is to say for administration by application at the surface of the keratin material under consideration, such a medium is considered in particular to be physiologically acceptable when it does not cause stinging, tightness or redness unacceptable to the user.

Essential Oil

Essential oils are products obtained from starting materials of plant origin (leaves, stems, flowers or whole plant, for example).

According to the definition given in the international standard ISO 9235 and adopted by the Commission of the European Pharmacopoeia, an essential oil is an odorous product, generally of complex composition, obtained from a botanically defined plant starting material, either by steam distillation, or by dry distillation, or by an appropriate mechanical process without heating (cold expression). The essential oil is generally separated from the aqueous phase via a physical process which does not result in any significant change in the composition.

Essential oils are generally volatile and liquid at ambient temperature, which distinguishes them from "set" oils. They are more or less coloured and their density is generally less than that of water. They have a high refractive index and most of them deflect polarized light. They are liposoluble and soluble in the usual organic solvents, steam distillable, and very sparingly soluble in water.

The essential oil of *Satureja montana* in accordance with the invention comprises more than 60% by weight of geraniol and more than 5% by weight of trans-β-caryophyllene.

It can be chosen from an essential oil of *Satureja montana* L. ssp. variegata or of any other variety having a similar chemotype.

An essential oil of *Satureja montana* L. ssp. variegata will in particular be used.

The essential oil of *Satureja montana* in accordance with the invention can advantageously be obtained from the aerial part of the plant.

Moreover, harvesting can be carried out at various stages of cutting: beginning of flowering or end of flowering and preferably at the end-of-flowering stage.

The choice of the technique for obtaining an essential oil depends mainly on the starting material: its original state and its characteristics, its nature proper. The "essential oil/plant raw material" yield may be extremely variable depending on the plants: 15 ppm to more than 20%. This choice determines the characteristics of the essential oil, in particular viscosity, colour, solubility, volatility, and richness or poorness in certain constituents.

Mention may be made, among the methods for obtaining an essential oil, of steam distillation, which can, for example, be carried out by dry distillation or hydrodistillation.

Hydrodistillation can be carried out on a glass apparatus, such as that defined in the European Pharmacopoeia for the determination of the essential oil from a plant material.

Steam distillation corresponds to the vaporization, in the presence of steam, of a substance which is not very miscible with water. The starting material is brought together with water brought to boiling point (hydrodistillation) or with steam in a still (dry distillation). The steam entrains the essential oil vapour, which is condensed in the condenser in order to be recovered as liquid phase in a Florentine flask (or essence jar), where the essential oil is separated from the water by settling. The term "aromatic water" or "hydrolat" or "distilled floral water" is used to describe the aqueous distillate which remains after the steam distillation, once the essential oil has been separated.

Advantageously, the essential oil in accordance with the invention is the essential oil of *Satureja montana* L. var. variegate (or *Satureja Montana* var. citrodoria oil).

The chemical composition of the essential oil of *Satureja montana* in accordance with the invention thus obtained can be analyzed by conventional techniques known to those skilled in the art, such as gas chromatography GC analysis, chromatographic analysis with flame ionization detection, referred to as GC-FID, or GC/MS analysis, which consists of the use of a mass spectrometer coupled to a gas chromatograph.

According to the invention, the geraniol is in a content of more than 65% by weight relative to the total weight of the constituents of said essential oil of *Satureja montana*, preferably greater than or equal to 70% by weight, and more preferentially from 70% to 85% by weight relative to the total weight of the constituents of the essential oil.

According to the invention, the trans-β-caryophyllene is in a content of more than 5% by weight relative to the total weight of the constituents of said essential oil of *Satureja montana*, preferably greater than or equal to 6% by weight, and more particularly from 6% to 10% by weight.

In terms of composition of the essential oil in accordance with the invention, the two major constituents are:
geraniol in a content of more than 65% by weight relative to the total weight of the constituents of the essential oil, preferably greater than or equal to 70% by weight, and more preferentially from 70% to 85% by weight relative to the total weight of the constituents of the essential oil;
trans-β-caryophyllene in a content of more than 5% by weight relative to the total weight of the constituents of the oil, preferably greater than or equal to 6% by weight, and more particularly from 6% to 10% by weight.

The following constituents are also present in concentrations greater than 0.35% by weight relative to the total weight of the constituents, in particular ranging from 0.5% to 5% by weight:
germacrene D,
nerol,
neral,
1-octen-3-ol,
geranial,
β-bisabolene.

The *Satureja montana* essential oil may be present in a cosmetic composition in a content of between 0.001% and 5%, in particular between 0.01% and 2%, and even more particularly between 0.1% and 1% by weight, relative to the total weight of the composition.

Cosmetic Composition

The cosmetic composition, in particular the deodorant composition, may comprise, in addition to the essential oil of *Satureja montana* L. ssp. variegata (or *Satureja Montana* var. citrodoria oil), any other essential oil capable of providing a fragrancing and/or antibacterial action. Among these, mention may in particular be made of basil, lemon catnip, citronella, clove, geranium, lemongrass, *Litsea cubeba*, lemon balm, oregano and thyme.

The deodorant cosmetic composition may also comprise, in addition to the essential oil of *Satureja montana* L. ssp. variegata at least one additional deodorant active agent and/or one antiperspirant active agent as defined hereinafter.

Deodorant Active Agents

The composition according to the invention can comprise one or more deodorant active agents, such as, for example:
- bacteriostatic agents or other bactericidal agents such as 2,4,4'-trichloro-2'-hydroxydiphenyl ether (triclosan), 2,4-dichloro-2'-hydroxydiphenyl ether, 3',4',5'-trichlorosalicylanilide, 1-(-3',4'-dichlorophenyl)-3-(4'-chlorophenyl)urea (triclocarban) or 3,7,11-trimethyldodeca-2,5,10-trienol (Farnesol); quaternary ammonium salts, for instance cetyltrimethylammonium salts, cetylpyridinium salts; chlorhexidine and salts; diglyceryl monocaprate, diglyceryl monolaurate or glyceryl monolaurate; polyhexamethylene biguanide salts;
- zinc salts, such as zinc salicylate, zinc phenolsulfonate, zinc pyrrolidonecarboxylate (more commonly known as zinc pidolate), zinc sulfate, zinc chloride, zinc lactate, zinc gluconate, zinc ricinoleate, zinc glycinate, zinc carbonate, zinc citrate, zinc chloride, zinc laurate, zinc oleate, zinc orthophosphate, zinc stearate, zinc tartrate, zinc lactate, zinc acetate or their mixtures thereof;
- odour absorbers, such as zeolites, cyclodextrins, metal oxide silicates, such as those described in Application US 2005/063928, metal oxide particles modified by a transition metal, such as described in Applications US 2005/084464 and US 2005/084474, aluminosilicates, such as those described in Application EP 1 658 863, or particles of chitosan derivatives, such as those described in U.S. Pat. No. 6,916,465;
- substances which block the enzymatic reactions responsible for the formation of odorous compounds, such as arylsulfatase, 5-lipoxygenase, aminocylase or β-glucuronidase inhibitors;

and mixtures thereof.

The deodorant active agents can be present in the composition according to the invention in a proportion of from 0.01% to 10% by weight and preferably in a proportion of from 0.1% to 5% by weight, relative to the total weight of the composition.

Antiperspirant Active Agents

The antiperspirant active agents are preferably chosen from aluminium and/or zirconium salts; complexes of zirconium hydroxychloride and of aluminium hydroxychloride with an amino acid, such as those described in U.S. Pat. No. 3,792,068, commonly known as "ZAG" complexes. Such complexes are generally known under the name ZAG (when the amino acid is glycine). The ZAG complexes ordinarily exhibit an Al/Zr quotient ranging from approximately 1.67 to 12.5 and a metal/CI quotient ranging from approximately 0.73 to 1.93. Mention may be made, among these products, of aluminium zirconium octachlorohydrex GLY, aluminium zirconium pentachlorohydrex GLY, aluminium zirconium tetrachlorohydrate GLY and aluminium zirconium trichlorohydrate GLY.

Mention may be made, among the aluminium salts, of aluminium chlorohydrate, aluminium chlorohydrex, aluminium chlorohydrex PEG, aluminium chlorohydrex PG, aluminium dichlorohydrate, aluminium dichlorohydrex PEG, aluminium dichlorohydrex PG, aluminium sesquichlorohydrate, aluminium sesquichlorohydrex PEG, aluminium sesquichlorohydrex PG, alum salts, aluminium sulfate, aluminium zirconium octachlorohydrate, aluminium zirconium pentachlorohydrate, aluminium zirconium tetrachlorohydrate, aluminium zirconium trichlorohydrate and more particularly the aluminium hydroxychloride sold by the company Reheis under the name Reach 301 or by the company Guilini Chemie under the name Aloxicoll PF 40. Aluminium zirconium salts are, for example, the product sold by the company Reheis under the name Reach AZP-908-SUF.

Use will more particularly be made of aluminium chlorohydrate in the activated or non-activated form.

The antiperspirant active agents can be present in the composition according to the invention in a proportion of from 0.001% to 30% by weight and preferably in a proportion of from 0.5% to 25% by weight, relative to the total weight of the composition.

Galenical Forms

The composition according to the invention can be provided in any galenical forms conventionally used for a topical application and in particular in the form of aqueous gels or of aqueous or aqueous/alcoholic solutions. They can also, by addition of a fatty or oily phase, be provided in the form of dispersions of the lotion type, of emulsions with a liquid or semi-liquid consistency of the milk type, obtained by dispersion of a fatty phase in an aqueous phase (O/W) or vice versa (W/O), or of suspensions or emulsions with a soft, semi-solid or solid consistency of the cream or gel type, or alternatively of multiple emulsions (W/O/W or O/W/O), of microemulsions, of vesicular dispersions of ionic and/or non-ionic type, or of wax/aqueous phase dispersions. These compositions are prepared according to the usual methods.

The compositions can in particular be packaged in pressurized form in an aerosol device or in a pump-dispenser bottle; packaged in a device equipped with a perforated wall, in particular a grate; packaged in a device equipped with a ball applicator ("roll-on"); packaged in the form of sticks or in the form of a loose or compacted powder. In this regard, they comprise the ingredients generally used in products of this type, which are well known to those skilled in the art.

According to another specific form of the invention, the compositions according to the invention can be anhydrous.

The term "anhydrous composition" is intended to mean a composition containing less than 2% by weight of water, indeed less than 0.5% of water, and in particular devoid of water, the water not being added during the preparation of the composition but corresponding to the residual water contributed by the mixed ingredients.

According to another particular form of the invention, the compositions according to the invention may be solid, in particular in stick form.

The term "solid composition" is intended to mean that the measurement of the maximum force measured by texturometry during the penetration of a probe into the sample of formula must be at least equal to 0.25 newtons, in particular at least equal to 0.30 newtons and in particular at least equal to 0.35 newtons, assessed under precise measurement conditions as follows.

The formulae are poured hot into jars with a diameter of 4 cm and a depth of 3 cm. Cooling is carried out at ambient temperature. The hardness of the formulae produced is measured after an interval of 24 hours. The jars containing the samples are characterized in texturometry using a texture analyzer, such as that sold by the company Rheo, TA-XT2, according to the following protocol: a probe of stainless-steel ball type with a diameter of 5 mm is brought into contact with the sample at a rate of 1 mm/s. The measurement system detects the interface with the sample, with a detection threshold equal to 0.005 newtons. The probe sinks 0.3 mm into the sample, at a rate of 0.1 mm/s. The measuring device records the change in the force measured in compression over time, during the penetration phase. The hardness of the sample corresponds to the mean of the maximum values of the force detected during the penetration, over at least 3 measurements.

Aqueous Phase

The compositions according to the invention intended for cosmetic use can comprise at least one aqueous phase. They are in particular formulated as aqueous lotions or as water-in-oil or oil-in-water emulsions or as multiple emulsions (oil-in-water-in-oil or water-in-oil-in-water triple emulsions (such emulsions are known and described, for example, by C. Fox in "Cosmetics and Toiletries"—November 1986—Vol. 101—pages 101-112)).

The aqueous phase of said compositions contains water and generally other water-soluble or water-miscible solvents. The water-soluble or water-miscible solvents comprise short-chain, for example $C_1$-$C_4$, monoalcohols, such as ethanol or isopropanol; diols or polyols, such as ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. Use will more particularly be made of propylene glycol and glycerol, and propane-1,3-diol.

The composition according to the invention preferably has a pH ranging from 3 to 9, according to the support chosen.

Emulsifiers

Oil-in-Water Emulsifiers

Mention may be made, as emulsifiers which can be used in the oil-in-water emulsions or oil-in-water-in-oil triple emulsions, for example, of non-ionic emulsifiers, such as oxyalkylenated (more particularly polyoxyethylenated) esters of fatty acids and of glycerol; oxyalkylenated esters of fatty acids and of sorbitan; oxyalkylenated (oxyethylenated and/or oxypropylenated) esters of fatty acids; oxyalkylenated (oxyethylenated and/or oxypropylenated) ethers of fatty alcohols; sugar esters, such as sucrose stearate; and mixtures thereof, such as the mixture of glyceryl stearate and PEG-40 stearate.

Mention may also be made of fatty alcohol/alkylpolyglycoside emulsifying mixtures, such as are described in Applications WO 92/06778, WO 95/13863 and WO 98/47610, for instance the commercial products sold by the company SEPPIC under the name Montanov®.

Water-in-Oil Emulsifiers

Among the emulsifers which can be used in the water-in-oil emulsions or water-in-oil-in-water-in-oil triple emulsions or triple emulsions, mention may be made, by way of example, of alkyl dimethicone copolyols, for instance Cetyl PEG/PPG-10/1 Dimethicone and more particularly the mixture Cetyl PEG/PPG-10/1 Dimethicone and Dimethicone (INCI name), such as the product sold under the trade name Abil EM90 by the company Goldschmidt, or alternatively the mixture (Polyglyceryl-4 stearate and Cetyl PEG/PPG-10 (and) Dimethicone (and) Hexyl Laurate), such as the product sold under the trade name Abil WE09 by the same company.

Among the water-in-oil emulsifiers, mention may also be made of dimethicone copolyols, for instance PEG-18/PPG-18 Dimethicone and more particularly the mixture Cyclopentasiloxane (and) PEG-18/PPG-18 Dimethicone (INCI name), such as the product sold by the company Dow Corning under the trade name Silicone DC 5225 C or KF-6040 from Shin-Etsu.

Among the water-in-oil emulsifiers, mention may also be made of non-ionic emulsifiers derived from fatty acids and polyols, alkyl polyglycosides (APGs), sugar esters and mixtures thereof.

As non-ionic emulsifiers derived from fatty acids and polyols, use may be made in particular of fatty acid esters of polyols, the fatty acid in particular containing a $C_8$-$C_{24}$ alkyl chain, and the polyols being, for example, glycerol and sorbitan.

Mention may in particular be made, as fatty acid esters of polyols, of isostearic acid esters of polyols, stearic acid esters of polyols, and mixtures thereof, in particular isostearic acid esters of glycerol and/or sorbitan.

Stearic acid esters of polyols that may in particular be mentioned include the polyethylene glycol esters, for instance PEG-30 Dipolyhydroxystearate, such as the product sold under the name Arlacel P135 by the company ICI.

Glycerol and/or sorbitan esters that may be mentioned, for example, include polyglyceryl isostearate, such as the product sold under the name Isolan GI 34 by the company Goldschmidt; sorbitan isostearate, such as the product sold under the name Arlacel 987 by the company ICI; sorbitan glyceryl isostearate, such as the product sold under the name Arlacel 986 by the company ICI, the mixture of sorbitan isostearate and polyglyceryl isostearate (3 mol) sold under the name Arlacel 1690 by the company Uniqema, and mixtures thereof.

The emulsifier can also be chosen from alkylpolyglycosides having an HLB of less than 7, for example those represented by the following general formula (1):

R—O-(G)$_x$         (1)

in which R represents a branched and/or unsaturated alkyl radical comprising from 14 to 24 carbon atoms, G represents a reduced sugar comprising 5 or 6 carbon atoms and x denotes a value ranging from 1 to 10 and preferably from 1 to 4, and G in particular denotes glucose, fructose or galactose.

The unsaturated alkyl radical can comprise one or more ethylenic unsaturations and in particular one or two ethylenic unsaturations.

As alkylpolyglycosides of this type, mention may be made of alkylpolyglucosides (G=glucose in formula (I)), and in particular the compounds of formula (I) in which R more particularly represents an oleyl radical (unsaturated C18 radical) or isostearyl (saturated C18 radical), G denotes glucose, x is a value ranging from 1 to 2, in particular isostearyl glucoside or oleyl glucoside, and mixtures thereof. This alkyl polyglucoside can be used as a mixture with a coemulsifier, more in particular with a fatty alcohol and in particular a fatty alcohol having the same fatty chain as that of the alkyl polyglucoside, that is to say comprising from 14 to 24 carbon atoms and having a branched and/or unsaturated chain, for example isostearyl alcohol when the alkyl polyglucoside is isostearyl glucoside and oleyl alcohol when the alkyl polyglucoside is oleyl glucoside, optionally in the form of a self-emulsifying composition, as described, for example, in document WO-A-92/06778. Use may be made, for example, of the mixture of isostearyl glucoside and isostearyl alcohol, sold under the name Montanov WO 18 by the company SEPPIC, and also the mixture of octyldodecanol and octyldodecyl xyloside sold under the name Fludanov 20X by the company SEPPIC.

Mention may also be made of succinic-terminated polyolefins, such as esterified succinic-terminated polyisobutylenes and their salts, in particular the diethanolamine salts, such as the products sold under the names Lubrizol 2724, Lubrizol 2722 and Lubrizol 5603 by the company Lubrizol or the commercial product Chemcinnate 2000.

The total amount of emulsifiers in the composition will preferably be, in the composition according to the invention, at active material contents ranging from 1% to 8% by weight and more particularly from 2% to 6% by weight, relative to the total weight of the composition.

Fatty Phase

The compositions according to the invention can comprise at least one water-immiscible organic liquid phase, known as fatty phase. This phase generally comprises one or more hydrophobic compounds which render said phase water-immiscible. Said phase is liquid (in the absence of structuring agent) at ambient temperature (20-25° C.). Preferentially, the water-immiscible organic liquid phase in accordance with the invention generally comprises at least one volatile oil and/or one non-volatile oil and optionally at least one structuring agent.

The term "oil" is intended to mean a fatty substance that is liquid at ambient temperature (25° C.) and atmospheric pressure (760 mmHg, i.e. 105 Pa). The oil may be volatile or non-volatile.

For the purposes of the invention, the term "volatile oil" is intended to mean an oil that is capable of evaporating on contact with the skin or the keratin fibre in less than one hour, at ambient temperature and atmospheric pressure. The volatile oils of the invention are volatile cosmetic oils which are liquid at ambient temperature and which have a non-zero vapour pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" is intended to mean an oil that remains on the skin or the keratin fibre at ambient temperature and atmospheric pressure for at least several hours, and that in particular has a vapour pressure of less than $10^{-3}$ mmHg (0.13 Pa).

The oil can be chosen from any physiologically acceptable oils and in particular cosmetically acceptable oils, in particular mineral, animal, vegetable or synthetic oils; in particular volatile or non-volatile hydrocarbon-based oils and/or silicone oils and/or fluoro oils, and mixtures thereof.

More specifically, the term "hydrocarbon-based oil" is intended to mean an oil mainly comprising carbon and hydrogen atoms and optionally one or more functions chosen from hydroxyl, ester, ether and carboxylic functions. Generally, the oil has a viscosity of from 0.5 to 100 000 mPa·s, preferably from 50 to 50 000 mPa·s and more preferably from 100 to 300 000 mPa·s.

Mention may be made, as examples of volatile oil which can be used in the invention, of:
volatile hydrocarbon-based oils chosen from hydrocarbon-based oils containing from 8 to 16 carbon atoms, and in particular $C_8$-$C_{16}$ isoalkanes of petroleum origin (also known as isoparaffins), for instance isododecane (also known as 2,2,4,4,6-pentamethylheptane), isodecane and isohexadecane, and for example the oils sold under the trade names Isopar or Permethyl, branched $C_8$-$C_{16}$ esters and isohexyl neopentanoate, and mixtures thereof. Use may also be made of other volatile hydrocarbon-based oils, such as petroleum distillates, in particular those sold under the name Shell Solt by the company Shell; and volatile linear alkanes, such as those described in Patent Application DE10 2008 012 457 from the company Cognis;
volatile silicones, for instance linear or cyclic volatile silicone oils, in particular those with a viscosity of 8 centistokes ($8 \times 10^{-6}$ m$^2$/s), and containing in particular from 2 to 7 silicon atoms, these silicones optionally comprising alkyl or alkoxy groups containing from 1 to 10 carbon atoms. Mention may in particular be made, as volatile silicone oils which can be used in the invention, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane or dodecamethylpentasiloxane;

and mixtures thereof.

Mention may also be made of the volatile linear alkyltrisiloxane oils of general formula (I):

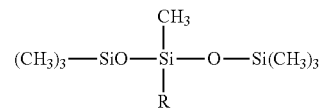

where R represents an alkyl group comprising from 2 to 4 carbon atoms, one or more hydrogen atoms of which may be replaced with a fluorine or chlorine atom.

Among the oils of general formula (I), mention may be made of:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

Mention may be made, as examples of non-volatile oil which can be used in the invention, of:
hydrocarbon-based oils of animal origin, such as perhydrosqualene;
vegetable hydrocarbon-based oils, such as liquid triglycerides of fatty acids containing 4 to 24 carbon atoms, such as heptanoic or octanoic acid triglycerides, or else wheat germ oil, olive oil, sweet almond oil, palm oil, rapeseed oil, cottonseed oil, alfalfa oil, poppy seed oil, pumpkin seed oil, cucumber oil, blackcurrant oil, evening primrose oil, millet oil, barley oil, *quinoa* oil, rye oil, safflower oil, candlenut oil, passionflower oil, musk rose oil, sunflower oil, maize oil, soybean oil, marrow oil, grape seed oil, sesame oil, hazelnut oil, apricot oil, macadamia oil, castor oil, avocado oil, caprylic/capric acid triglycerides, such as those sold by the company Stearineries Dubois or those sold under the names Miglyol 810, 812 and 818 by the company Dynamit Nobel, jojoba oil or shea butter oil;
linear or branched hydrocarbons of mineral or synthetic origin, such as liquid paraffins and derivatives thereof, petroleum jelly, polydecenes, polybutenes, hydrogenated polyisobutene, such as Parleam, or squalane;

synthetic ethers containing from 10 to 40 carbon atoms;

synthetic esters, in particular of fatty acids, for instance the oils of formula $R_1COOR_2$ in which $R_1$ represents the residue of a linear or branched higher fatty acid containing from 1 to 40 carbon atoms and $R_2$ represents a hydrocarbon-based chain, which is in particular branched, containing from 1 to 40 carbon atoms, with $R_1+R_2 \geq 10$, for instance purcellin oil (cetostearyl octanoate), isononyl isononanoate, isopropyl myristate, isopropyl palmitate, $C_{12}$ to $C_{15}$ alkyl benzoate, hexyl laurate, diisopropyl adipate, isononyl isononanoate, 2-ethylhexyl palmitate, 2-octyldodecyl stearate, 2-octyldodecyl erucate, isostearyl isostearate or tridecyl trimellitate; alcohol or polyalcohol octanoates, decanoates or ricinoleates, for instance propylene glycol dioctanoate; hydroxylated esters, for instance isostearyl lactate, octyl hydroxystearate, octyldodecyl hydroxystearate, diisostearyl malate, triisocetyl citrate, and fatty alcohol heptanoates, octanoates or decanoates; polyol esters, for instance propylene glycol dioctanoate, neopentyl glycol diheptanoate or diethylene glycol diisononanoate; and pentaerythritol esters, for instance pentaerythrityl tetraisostearate;

fatty alcohols which are liquid at ambient temperature and which comprise a branched and/or unsaturated carbon-based chain containing from 12 to 26 carbon atoms, such as octyldodecanol, isostearyl alcohol, 2-butyloctanol, 2-hexyldecanol, 2-undecylpentadecanol or oleyl alcohol;

higher fatty acids, such as oleic acid, linoleic acid or linolenic acid;

carbonates;

acetates;

citrates;

fluoro oils which are optionally partially hydrocarbon-based and/or silicone-based, for example fluorosilicone oils, fluoropolyethers or fluorinated silicones, such as described in document EP-A-847 752;

silicone oils, such as non-volatile linear or cyclic polydimethylsiloxanes (PDMSs); polydimethylsiloxanes comprising alkyl, alkoxy or phenyl groups which are pendent or at the end of the silicone chain, which groups have from 2 to 24 carbon atoms; or phenylated silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates, and mixtures thereof.

Additives

The cosmetic compositions according to the invention can also comprise cosmetic adjuvants chosen from emollients, antioxidants, opacifying agents, stabilizing agents, moisturizing agents, vitamins, bactericides, preservatives, polymers, fragrances, a structuring agent for a fatty phase, in particular chosen from waxes, pasty compounds, and inorganic or organic lipophilic gelling agents; organic or inorganic fillers; thickening or suspending agents, propellants or any other ingredient normally used in cosmetics for this type of application.

Of course, those skilled in the art will take care to choose this or these optional additional compounds so that the advantageous properties intrinsically attached to the cosmetic composition in accordance with the invention are not, or not substantially, detrimentally affected by the envisaged addition or additions.

Wax(es)

The wax is generally a lipophilic compound which is solid at ambient temperature (25° C.), which exhibits a reversible solid/liquid change in state and which has a melting point of greater than or equal to 30° C. which can range up to 200° C. and in particular up to 120° C.

In particular, the waxes suitable for the invention can exhibit a melting point of greater than or equal to 45° C. and in particular of greater than or equal to 55° C.

For the purposes of the invention, the melting point corresponds to the temperature of the most endothermic peak observed in thermal analysis (DSC) as described in the standard ISO 11357-3; 1999. The melting point of the wax may be measured using a differential scanning calorimeter (DSC), for example the calorimeter sold under the name MDSC 2920 by the company TA Instruments.

The measurement protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and it is finally subjected to a second temperature rise ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The waxes that may be used in the compositions according to the invention are chosen from waxes that are solid at ambient temperature of animal, plant, mineral or synthetic origin, and mixtures thereof.

As illustrations of waxes that are suitable for the invention, mention may be made in particular of hydrocarbon waxes, for instance beeswax, lanolin wax, Chinese insect waxes, rice bran wax, carnauba wax, candelilla wax, ouricury wax, esparto wax, berry wax, shellac wax, Japan wax and sumac wax; montan wax, orange wax and lemon wax, refined sunflower wax sold under the name Sunflower Wax by Koster Keunen, microcrystalline waxes, paraffins and ozokerite; polyethylene waxes, the waxes obtained by the Fischer-Tropsch synthesis and waxy copolymers, and also esters thereof.

Mention may also be made of waxes obtained by catalytic hydrogenation of animal or vegetable oils having linear or branched $C_8$-$C_{32}$ fatty chains. Mention may in particular be made, among these waxes, of isomerized jojoba oil, such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane) tetrastearate, sold under the name Hest 2T-45® by the company Heterene.

Mention may also be made of silicone waxes ($C_{30-45}$ alkyl dimethicone) or fluorinated waxes.

Use may also be made of the waxes obtained by hydrogenation of castor oil esterified with cetyl alcohol, sold under the names Phytowax Castor 16L64® and 22L73® by the company Sophim. Such waxes are described in Application FR-A-2 792 190.

As wax, use may be made of a $C_{20}$-$C_{40}$ alkyl (hydroxystearyloxy)stearate (the alkyl group comprising from 20 to 40 carbon atoms), alone or as a mixture.

Such a wax is sold in particular under the names Kester Wax K 82 P®, Hydroxypolyester K 82 P® and Kester Wax K 80 P® by the company Koster Keunen.

As microwaxes that may be used in the compositions according to the invention, mention may be made in particular of carnauba microwaxes, such as the product sold under the name MicroCare 350® by the company Micro Powders, microwaxes of synthetic wax, such as the product sold under the name MicroEase 114S® by the company Micro Powders, microwaxes consisting of a mixture of carnauba wax and polyethylene wax, such as the products sold under the names Micro Care 300® and 310® by the company Micro Powders, microwaxes consisting of a mixture of carnauba wax and synthetic wax, such as the product sold under the name Micro Care 325® by the company Micro Powders, polyethylene microwaxes, such as the products sold under the names Micropoly 200®, 220®, 220L® and 250S® by the company Micro Powders, the commercial products Performalene 400 Polyethylene and Performalene 500-L Polyethylene from New Phase Technologies, Performalene 655 Polyethylene or paraffin waxes, for instance the wax having the INCI name Microcrystalline Wax and Synthetic Wax and sold under the trade name Microlease by the company Sochibo; polytetrafluoroethylene microwaxes, such as those sold under the names Microslip 519® and 519 L® by the company Micro Powders.

Pasty Compounds

For the purposes of the present invention, the term "pasty compound" is intended to mean a lipophilic fatty compound which exhibits a reversible solid/liquid change of state, which exhibits, in the solid state, an anisotropic crystal arrangement and which comprises, at the temperature of 23° C., a liquid fraction and a solid fraction.

The pasty compound is preferably chosen from synthetic compounds and compounds of plant origin. A pasty compound can be obtained by synthesis from starting products of plant origin.

The pasty compound may be advantageously chosen from:
lanolin and derivatives thereof,
polymeric or non-polymeric silicone compounds,
polymeric or non-polymeric fluorinated compounds,
vinyl polymers, in particular:
olefin homopolymers,
olefin copolymers,
hydrogenated diene homopolymers and copolymers,
linear or branched oligomers, homopolymers or copolymers of alkyl (meth)acrylates preferably containing a $C_8$-$C_{30}$ alkyl group,
homo- and copolymeric oligomers of vinyl esters having $C_8$-$C_{30}$ alkyl groups, and
homo- and copolymeric oligomers of vinyl ethers having $C_8$-$C_{30}$ alkyl groups,
liposoluble polyethers resulting from polyetherification between one or more $C_2$-$C_{100}$, preferably $C_2$-$C_{50}$, diols,
esters,
mixtures thereof.

Among the esters, the following are in particular preferred:
esters of a glycerol oligomer, in particular diglycerol esters, in particular condensates of adipic acid and of glycerol, for which some of the hydroxyl groups of the glycerols have reacted with a mixture of fatty acids such as stearic acid, capric acid, stearic acid and isostearic acid and 12-hydroxystearic acid, in particular such as those sold under the brand name Softisan 649 by the company Sasol,
the arachidyl propionate sold under the Waxenol 801 brand by Alzo,
phytosterol esters,
fatty acid triglycerides and derivatives thereof,
pentaerythritol esters,
non-crosslinked polyesters resulting from the polycondensation between a linear or branched $C_4$-$C_{50}$ dicarboxylic acid or polycarboxylic acid and a $C_2$-$C_{50}$ diol or polyol,
aliphatic esters of an ester resulting from the esterification of an aliphatic hydroxycarboxylic acid ester by an aliphatic carboxylic acid,
polyesters resulting from the esterification, by a polycarboxylic acid, of an aliphatic hydroxycarboxylic acid ester, said ester comprising at least two hydroxyl groups, such as the products Risocast DA-H® and Risocast DA-L®,
esters of dimer diol and dimer diacid, if appropriate esterified on their free alcohol or acid functional group(s) by acid or alcohol radicals, such as Plandool-G,
mixtures thereof.

Inorganic Lipophilic Gelling Agents

Inorganic lipophilic gelling agents that may be mentioned include optionally modified clays, for instance hectorites modified with a $C_{10}$ to $C_{22}$ ammonium chloride, for instance hectorite modified with distearyldimethylammonium chloride, for instance the product sold under the name Bentone 38V® by the company Elementis.

Mention may also be made of fumed silica optionally hydrophobically treated at the surface, the size of the particles of which is less than 1 μm. This is because it is possible to chemically modify the surface of the silica by chemical reaction which results in a decrease in the number of silanol groups present at the surface of the silica. Silanol groups can in particular be replaced by hydrophobic groups: a hydrophobic silica is then obtained. The hydrophobic groups can be trimethylsiloxyl groups, which are obtained in particular by treatment of fumed silica in the presence of hexamethyldisilazane. Silicas thus treated are named "Silica silylate" according to the CTFA (8th edition, 2000). They are, for example, sold under the references Aerosil R812® by Degussa, Cab-O-Sil TS-530® by the company Cabot, dimethylsilyloxyl or polydimethylsiloxane groups, which are obtained in particular by treatment of fumed silica in the presence of polydimethylsiloxane or dimethyldichlorosilane. Silicas thus treated are named "Silica dimethyl silylate" according to the CTFA (8th edition, 2000). They are, for example, sold under the references Aerosil R972® and Aerosil R974® by the company Degussa and Cab-O-Sil TS-610® and Cab-O-Sil TS-720® by the company Cabot.

The hydrophobic fumed silica in particular has a particle size that may be nanometric to micrometric, for example ranging from about 5 to 200 nm.

Organic Lipophilic Gelling Agents

The polymeric organic lipophilic gelling agents are, for example, partially or totally crosslinked elastomeric organopolysiloxanes of three-dimensional structure, for instance those sold under the names KSG6®, KSG16® and KSG18® by the company Shin-Etsu, Trefil E-505C® and Trefil E-506C® by the company Dow Corning, Gransil SR-CYC®, SR DMF10®, SR-DC556®, SR 5CYC Gel®, SR DMF 10 Gel® and SR DC 556 Gel® by the company Grant Industries and SF 1204® and JK 113® by the company General Electric; ethylcellulose, for instance the product sold under the name Ethocel® by the company Dow Chemical; galactomannans comprising from one to six and in particular from two to four hydroxyl groups per monosaccharide, substituted with a saturated or unsaturated alkyl chain, for instance guar gum alkylated with $C_1$ to $C_6$, and in particular $C_1$ to $C_3$, alkyl chains, and mixtures thereof. Block copolymers of "diblock", "triblock" or "radial" type of the polystyrene/polyisoprene or polystyrene/polybutadiene type, such as those sold under the name Luvitol HSB® by the company BASF, of the polystyrene/copoly(ethylene-propylene) type, such as those sold under the name Kraton® by the company Shell Chemical Co., or alternatively of the polystyrene/copoly(ethylene-butylene) type, or blends of triblock and radial (star) copolymers in isododecane, such as those sold by the company Penreco under the name Versagel®, such as, for example, the blend of butylene/ethylene/styrene triblock copolymer and of ethylene/propylene/styrene star copolymer in isododecane (Versagel M 5960).

Mention may also be made, among the lipophilic gelling agents which can be used in the compositions according to the invention, of esters of dextrin and of fatty acid, such as dextrin palmitates, in particular such as those sold under the names Rheopearl TL® or Rheopearl KL® by the company Chiba Flour.

Use may also be made of silicone polyamides of the polyorganosiloxane type, such as those described in documents U.S. Pat. Nos. 5,874,069, 5,919,441, 6,051,216 and 5,981,680.

Thickeners and Suspending Agents

The thickeners can be chosen from carboxyvinyl polymers, such as the Carbopols (Carbomers) and the Pemulens (acrylate/$C_{10}$-$C_{30}$ alkyl acrylate copolymer); polyacrylamides, such as, for example, the crosslinked copolymers sold under the names Sepigel 305 (CTFA name: polyacrylamide/C13-14 isoparaffin/laureth 7) or Simulgel 600 (CTFA name: acrylamide/sodium acryloyldimethyltaurate copolymer/isohexadecane/polysorbate 80) by the company Seppic; optionally crosslinked and/or neutralized polymers and copolymers of 2-acrylamido-2-methylpropanesulfonic acid, such as the poly(2-acrylamido-2-methylpropanesulfonic acid) sold by the company Hoechst under the trade name Hostacerin AMPS (CTFA name: ammonium polyacryloyldimethyltaurate) or Simulgel 800, sold by the company Seppic (CTFA name: sodium polyacryloyldimethyltaurate/polysorbate 80/sorbitan oleate); copolymers of 2-acrylamido-2-methylpropanesulfonic acid and of hydroxyethyl acrylate, such as Simulgel NS and Sepinov EMT 10, sold by the company Seppic; cellulose derivatives, such as hydroxyethylcellulose or cetyl hydroxyethylcellulose; polysaccharides and in particular gums, such as xanthan gum or hydroxypropyl guar gums; or silicas, such as, for example, Bentone Gel MIO, sold by the company NL Industries, or Veegum Ultra, sold by the company Polyplastic.

The thickeners can also be cationic, such as, for example, Polyquaternium-37, sold under the name Salcare SC95 (Polyquaternium-37 (and) Mineral Oil (and) PPG-1 Trideceth-6) or Salcare SC96 (Polyquaternium-37 (and) Propylene Glycol Dicaprylate/Dicaprate (and) PPG-1 Trideceth-6), or other crosslinked cationic polymers, such as, for example, those having the CTFA name Ethyl Acrylate/Dimethylaminoethyl Methacrylate Cationic Copolymer In Emulsion.

Organic Powder

According to one particular form of the invention, the compositions according to the invention will additionally comprise an organic powder.

In the present application, the term "organic powder" is intended to mean any solid which is insoluble in the medium at ambient temperature (25° C.).

As organic powders that may be used in the composition of the invention, examples that may be mentioned include polyamide particles and in particular those sold under the Orgasol names by the company Atochem; nylon-6,6 fibres, in particular the polyamide fibres sold by Etablissements P Bonte under the name Polyamide 0.9 Dtex 0.3 mm (INCI name: Nylon 6,6 or Polyamide 6,6) having a mean diameter of 6 µm, a weight of approximately 0.9 dtex and a length ranging from 0.3 mm to 1.5 mm; polyethylene powders; microspheres based on acrylic copolymers, such as those made of ethylene glycol dimethacrylate/lauryl methacrylate copolymer sold by the company Dow Corning under the name of Polytrap; polymethyl methacrylate microspheres, sold under the name Microsphere M-100 by the company Matsumoto or under the name Covabead LH85 by the company Wackherr; hollow polymethyl methacrylate microspheres (particle size: 6.5-10.5µ) sold under the name Ganzpearl GMP 0800 by Ganz Chemical; methyl methacrylate/ethylene glycol dimethacrylate copolymer microbeads (size: 6.5-10.5µ) sold under the name Ganzpearl GMP 0820 by Ganz Chemical or Microsponge 5640 by the company Amcol Health & Beauty Solutions; ethylene-acrylate copolymer powders, such as those sold under the name Flobeads by the company Sumitomo Seika Chemicals; expanded powders such as hollow microspheres and in particular microspheres formed from a terpolymer of vinylidene chloride, acrylonitrile and methacrylate and sold under the name Expancel by the company Kemanord Plast under the references 551 DE 12 (particle size of about 12 µm and mass per unit volume of 40 kg/m$^3$), 551 DE 20 (particle size of about 30 µm and mass per unit volume of 65 kg/m$^3$), 551 DE 50 (particle size of about 40 µm), or the microspheres sold under the name Micropearl F 80 ED by the company Matsumoto; powders of natural organic materials such as starch powders, in particular of crosslinked or non-crosslinked corn, wheat or rice starch, such as the powders of starch crosslinked with octenylsuccinic anhydride, sold under the name Dry-Flo by the company National Starch; silicone resin microbeads such as those sold under the name Tospearl by the company Toshiba Silicone, in particular Tospearl 240; amino acid powders such as the lauroyllysine powder sold under the name Amihope LL-11 by the company Ajinomoto; particles of wax microdispersion, which preferably have mean sizes of less than 1 µm and in particular ranging from 0.02 µm to 1 µm, and which are formed essentially from a wax or a mixture of waxes, such as the products sold under the name Aquacer by the company Byk Cera, and in particular: Aquacer 520 (mixture of synthetic and natural waxes), Aquacer 514 or 513 (polyethylene wax) or Aquacer 511 (polymer wax), or such as the products sold under the name Jonwax 120 by Johnson Polymer (mixture of polyethylene and paraffin waxes) and under the name Ceraflour 961 by the company Byk Cera (micronized modified polyethylene wax); and mixtures thereof.

Suspending Agents

In order to improve the homogeneity of the product, use may additionally be made of one or more suspending agents which are preferably chosen from hydrophobic modified montmorillonite clays, such as hydrophobic modified bentonites or hectorites. Mention may be made, for example, of the product Stearalkonium Bentonite (CTFA name) (reaction product of bentonite and of the quaternary ammonium stearalkonium chloride), such as the commercial product sold under the name Tixogel MP 250 by the company Sud Chemie Rheologicals, United Catalysts Inc., or the product Disteardimonium Hectorite (CTFA name) (reaction product of hectorite and of distearyldimonium chloride), sold under the name Bentone 38 or Bentone Gel by the company Elementis Specialities.

Other suspending agents can be used, in this case in hydrophilic (aqueous and/or ethanolic) media. They can be derivatives of cellulose, xanthan, guar, starch, locust bean or agar agar.

The suspending agents are preferably present in amounts ranging from 0.1% to 5% by weight and more preferentially from 0.2% to 2% by weight relative to the total weight of the composition.

The amounts of these various constituents which can be present in the cosmetic composition according to the invention are those conventionally used in compositions for the treatment of perspiration.

Aerosols

The compositions according to the invention can also be pressurized and be packaged in an aerosol device made up of:
(A) a container comprising an antiperspirant composition as defined previously,
(B) at least one propellant and one means for dispensing said aerosol composition.

The propellants generally used in products of this type, which are well known to those skilled in the art, are, for example, dimethyl ether (DME); volatile hydrocarbons, such as n-butane, propane or isobutane, and mixtures thereof, optionally with at least one chlorinated and/or fluorinated hydrocarbon; mention may be made, among the latter, of the compounds sold by the company DuPont de Nemours under the names Freon® and Dymel®, and in particular monofluorotrichloromethane, difluorodichloromethane, tetrafluorodichloroethane and 1,1-difluoroethane, sold in particular under the trade name Dymel 152 A by the company DuPont. Use may also be made, as propellant, of carbon dioxide gas, nitrous oxide, nitrogen or compressed air.

The compositions comprising perlite particles as defined above and the propellant(s) can be in the same compartment or in different compartments in the aerosol container. According to the invention, the concentration of propellant generally varies from 5% to 95% by weight pressurized and more preferentially from 50% to 85% by weight, relative to the total weight of the pressurized composition.

The dispensing means, which forms a part of the aerosol device, is generally formed by a dispensing valve controlled by a dispensing head, which itself comprises a nozzle via which the aerosol composition is vaporized. The container comprising the pressurized composition can be opaque or transparent. It can be made of glass, of polymer or of metal, optionally covered with a protective lacquer layer.

The terms "between . . . and . . . " and "ranging from . . . to . . . " should be understood as being limits inclusive, unless otherwise mentioned.

The examples which follow illustrate the present invention without limiting the scope thereof.

EXAMPLE 1

An essential oil of lemon sariette (*Satureja montana* L. ssp. variegata or *Satureja montana* citrodoria oil) was prepared from the aerial part of the plant at the end-of-flowering stage by distillation of 8 kg by fresh weight by steam distillation in a 50 litre distillation device. Yield obtained about 0.53%

The essential oil obtained comprises, as major constituents

| | |
|---|---|
| Geraniol | 75.5% by weight |
| Trans-β-caryophyllene | 8.8% by weight |
| Germacrene D | 2.6% by weight |
| Nerol | 2.7% by weight |
| Neral | 1.2% by weight |
| Geranial | 0.9% by weight |
| 1-Octen-3-ol | 1.3% by weight |
| Beta-bisabolene | 0.8% by weight. |

The composition of the essential oil obtained was determined by GC and mass spectrometry.

Test for Activity of the Essential Oil of *Satureia montana* L. Var. *Variegata* (or *Satureia montana* Citrodoria Oil) on Inhibition of the Microorganism *Cornebacterium xerosis* (CIP 52.16)

The essential oil of *Satureja montana* L. ssp. variegata used in the present example was dispersed in a dilute agar gel.

Principle:

The aim of this test is to more particularly determine the activity of a composition comprising an essential oil in accordance with the invention with respect to the microorganism Cornebacterium xerosis, derived from the Collection of the Institut Pasteur 52.16, implicated in phenomena associated with the development of unpleasant underarm odours, this microorganism being placed under optimal growth conditions.

Protocol:

By a method of dilution in a liquid medium, various concentrations of the *Satureja montana* L. ssp. variegata essential oil are brought into contact with a nutritive broth inoculated with the test strain. After incubation, the surviving microorganisms are counted (log).

Preparation of the composition comprising the essential oil of *Satureja montana* L. ssp. variegata (or *Satureja montana* citrodoria oil) subjected to the test: a stock solution at 10% in 1% agar is prepared.

The essential oil of *Satureja montana* L. ssp. variegata (or *Satureja montana* citrodoria oil) is brought into contact, at a concentration that is double the test concentration, with a doubly concentrated nutritive broth containing a titre of approximately between 2 and $6.10^5$ CFU/ml. The preparation is thus mixed at 50/50 with the C. xerosis culture broth.

After incubating at 32.5° C.±2.5° C. for 24 h, the surviving microorganisms are counted by spiral inoculation and compared with the starting inoculum in order to define the degrees of reduction obtained. A value of 5.2 log is assigned to the initial inoculum.

Spiral inoculation systems use a semi-automatic inoculator of the AES® or Interscience® type, which deposits a calibrated volume of a liquid sample at the surface of an agar placed on a rotating plate, while describing an Archimedean spiral. After incubation, reading is carried out using graphs. This technique makes it possible to carry out the bacterial count of a sample on one and the same dish, dispensing with all or some of the intermediate dilutions. This methodology is much used and is an officially accepted technique.

Operating Conditions:

Concentrations of essential oil of *Satureja montana* L. ssp. variegata (or *Satureja montana* citrodoria oil) tested: 0.1%, 0.5% and 1% (v/v or w/v).

Diluant used: 1% agar.

Appearance in the product in the broth: opaque emulsion.

Results:

After having inoculated approximately 5.2 log into the medium containing various concentrations of the essential oil, a decontamination of about 3.3 log of the bacterial population was obtained right from 0.1% after 24 hours, and total decontamination of the bacterial population was obtained right from 0.5% after 24 hours.

| Sample tested | Starting inoculum | Contact time | Concentration | | |
|---|---|---|---|---|---|
| | | | 0.1% | 0.5% | 1% |
| Solution comprising an essential oil of lemon savory | 5.2 | | 1.9 | | |

The essential oil of lemon savory can therefore be used in a composition which thus makes it possible to inhibit the growth of *Corynebacterium xerosis*, of use for the treatment of unpleasant odours produced by the decomposition of sweat.

EXAMPLE 2

Deodorant Formula: Aerosol

| | |
|---|---|
| Essential oil according to Example 1 | 0.5% |
| Triclosan | 0.75% |
| Silicone | 3% |
| Fragrance | 0.75% |
| Isobutane and propane | 45% |
| Ethyl alcohol | q.s. for 100% |

EXAMPLE 3

Antiperspirant and Deodorant Formula

| | |
|---|---|
| Essential oil according to Example 1 | 0.5% |
| Aluminium Hydrochloride | 25% |
| Silicone | 1.25% |
| Fragrance | 0.7% |
| Water | q.s. for 100% |

Comparative Tests Between Two Sariette Essential Oils

The relative intensity and the olfactive profile of the smell produced by each of the following essential oils were evaluated:
  Lemon sariette essential oil (*Satureja montana* L. ssp. variegata or *Satureja montana* citrodoria oil) according to example 1;
  Mountain sariette essential oil (*Satureja montana* oil) comprising from 10 to 18')/0 of para-cymene, from 0.2 to 2% limonene, from 8 to 18% of γ-terpinene, from 22 to 30% of carvacrol, from 12 to 20% of thymol and from 2 to 4% de β-caryophyllene
Protocol:
  The smell of each of sariette essential oils was evaluated by a panel of 10 trained experts which had previously evaluated blindly 30 essential oils diluted at 1% in an oil of Capric/Caprylic Triglyceride in order to have a clear perception but nevertheless not too intense and to be able to compare both sariette essential oils in term of relative intensity. A questionnaire was handed to each. They established their olfactive profiles.

The relative intensity of the smell produced by each essential oil was noted on a scale from 0 to 5: 0 corresponds to the absence of perceived smell and 5 to a very strong smell.

| Evaluated smell | *Satureja montana* L. ssp. *Variegata* (or *Satureja montana* citrodoria oil) | *Satureja montana* oil |
|---|---|---|
| Relative Intensity | 3.6 | 4 |
| Olfactive profile | Aromatic - Hesperides (lemonated) Floral (rose), green, woody, spicy | Aromatic Phénolic Green, woody, spicy |

The experts concluded that the essential oil of *Satureja montana* L. ssp. variegata oil (or *Satureja montana* citrodoria oil) produced a less intense and more pleasant smell than the one produced by the essential oil of *Satureja montana* oil.

The invention claimed is:

1. A cosmetic method for treating human body odours which comprises applying to human keratin materials, a composition comprising a cosmetically acceptable medium and as a deodorant active agent, an essential oil of *Satureja montana* comprising more than 65% by weight of geraniol and more than 5% by weight of trans-β-caryophyllene relative to the total weight of the constituents of the essential oil, wherein the essential oil of *Satureja montana* is present in the composition in a content of between 0.001% and 5% relative to the total weight of the composition.

2. The cosmetic method according to claim 1, in which the geraniol is present in a content greater than or equal to 70% by weight relative to the total weight of the constituents of the essential oil.

3. The cosmetic method according to claim 1, in which the trans-β-caryophyllene is present in a content greater than or equal to 6% by weight relative to the total weight of the constituents of the essential oil.

4. The cosmetic method according to claim 3, in which the geraniol is present in the composition in a content greater than or equal to 70% by weight relative to the total weight of the constituents of the essential oil.

5. The cosmetic method according to claim 1, in which each of the following constituents is present in a content greater than or equal to 0.35% by weight, relative to the total weight of the constituents of the essential oil:
  germacrene D,
  nerol,
  neral,
  1-octen-3-ol,
  geranial,
  β-bisabolene.

6. The cosmetic method according to claim 1, wherein the essential oil is an essential oil of *Satureja montana* L. ssp. *variegate*.

7. The cosmetic method according to claim 1, wherein the essential oil of *Satureja montana* is obtained from an aerial part of a plant.

8. The cosmetic method according to claim 1 where the essential oil of *Satureja montana* is present in the composition in a content of between 0.01% and 2% relative to the total weight of the composition.

9. The cosmetic method according to claim 1, wherein the essential oil of *Satureja montana* acts as an antibacterial agent for treating human body odours caused by *Corynebacterium xerosis*.

* * * * *